US012048803B2

(12) United States Patent
Trummer et al.

(10) Patent No.: US 12,048,803 B2
(45) Date of Patent: Jul. 30, 2024

(54) INHALER

(71) Applicant: SOCIETE INDUSTRIELLE DE SONCEBOZ SA, Sonceboz (CH)

(72) Inventors: Herbert Trummer, Worben (CH); Nicolas Bailo, Nidau (CH); Olivier Pajot, Belmont-sur-Lausanne (CH); Denis Tilloy, Sonceboz (CH); Guillaume Verez, Lausanne (CH)

(73) Assignee: SOCIETE INDUSTRIELLE DE SONCEBOZ SA, Sonceboz (CH)

( * ) Notice: Subject to any disclaimer, the term of this patent is extended or adjusted under 35 U.S.C. 154(b) by 943 days.

(21) Appl. No.: 17/047,823

(22) PCT Filed: May 7, 2019

(86) PCT No.: PCT/EP2019/061712
§ 371 (c)(1),
(2) Date: Oct. 15, 2020

(87) PCT Pub. No.: WO2019/215173
PCT Pub. Date: Nov. 14, 2019

(65) Prior Publication Data
US 2021/0154418 A1    May 27, 2021

(30) Foreign Application Priority Data
May 8, 2018 (EP) .................................... 18171361

(51) Int. Cl.
*A61M 15/00* (2006.01)
(52) U.S. Cl.
CPC .... *A61M 15/0006* (2014.02); *A61M 15/0035* (2014.02); *A61M 2202/064* (2013.01); *A61M 2205/3331* (2013.01)

(58) Field of Classification Search
CPC ..... A61M 15/00–0001; A61M 15/0005–0008; A61M 15/002–0021;
(Continued)

(56) References Cited

U.S. PATENT DOCUMENTS

| 2008/0257348 A1* | 10/2008 | Piper ................. A61M 16/0069 128/205.25 |
| 2009/0178672 A1* | 7/2009 | Mullinger ............ A61M 15/00 128/200.14 |

(Continued)

FOREIGN PATENT DOCUMENTS

| GB | 2354451 | 3/2001 |
| WO | 94/08552 | 4/1994 |
| WO | 99/27987 | 6/1999 |

OTHER PUBLICATIONS

International Search Report and Written Opinion issued by the International Searching Authority, dated Jun. 14, 2019, for International Patent Application No. PCT/EP2019/061712; 17 pages.

*Primary Examiner* — Rachel T Sippel
(74) *Attorney, Agent, or Firm* — Faegre Drinker Biddle & Reath LLP

(57) ABSTRACT

Inhaler for oral inhalation administration of a drug, comprising a housing, a drug chamber in the housing, an air pump configured to pump air through the drug chamber for expulsing the drug through an outlet of a mouthpiece, wherein the air pump comprises a motor coupled to a centrifugal compressor operable to pump air through the drug chamber at a pressure greater than 30 millibars and a flow rate greater than 25 litres per minute.

22 Claims, 9 Drawing Sheets

(58) Field of Classification Search
CPC ... A61M 15/0028–003; A61M 15/0033–0041;
A61M 15/0091; A61M 15/0095–0096
See application file for complete search history.

(56) References Cited

U.S. PATENT DOCUMENTS

| | | | |
|---|---|---|---|
| 2011/0097222 A1* | 4/2011 | Komatsu | F04D 29/5853 |
| | | | 417/366 |
| 2011/0297153 A1* | 12/2011 | Grimsey | B63C 11/24 |
| | | | 128/204.18 |
| 2014/0306460 A1* | 10/2014 | Donnelly | F02C 7/32 |
| | | | 290/1 A |
| 2015/0104335 A1* | 4/2015 | Faller | F04D 29/5806 |
| | | | 417/244 |
| 2015/0335851 A1* | 11/2015 | Cullen | A61M 16/209 |
| | | | 128/204.25 |
| 2018/0064894 A1 | 3/2018 | Fu | |
| 2019/0060586 A1* | 2/2019 | Holakovsky | A61M 15/0041 |
| 2021/0003171 A1* | 1/2021 | Tangudu | F16C 32/0461 |

* cited by examiner

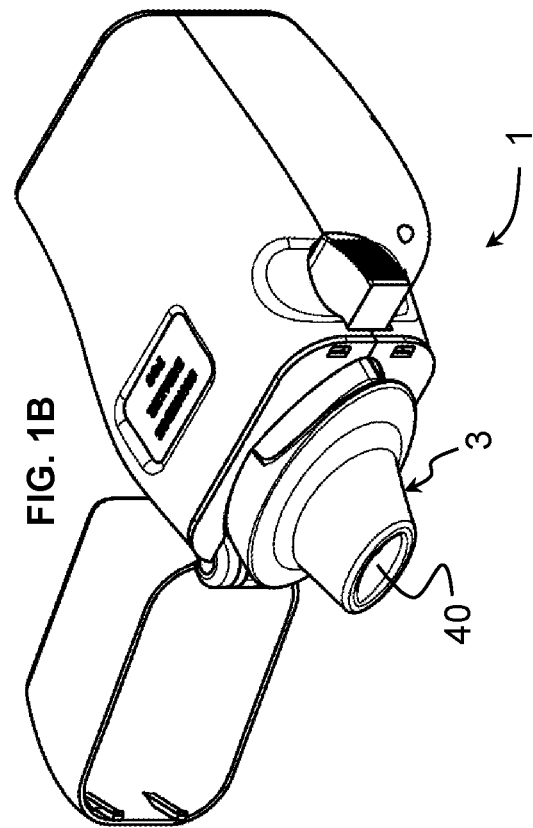
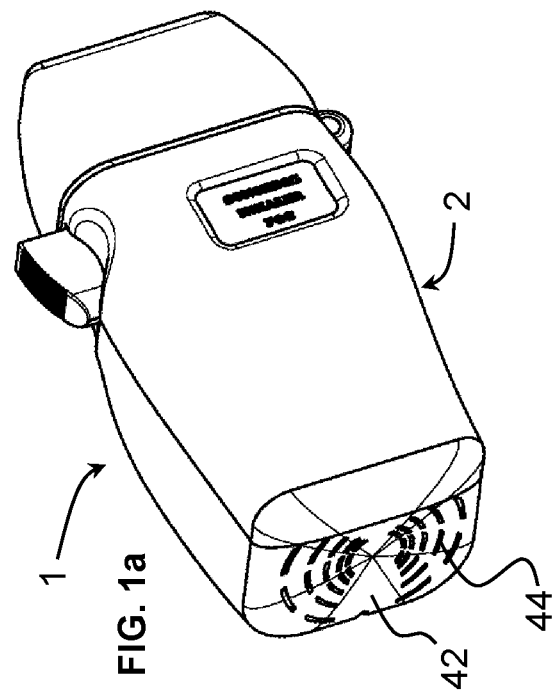
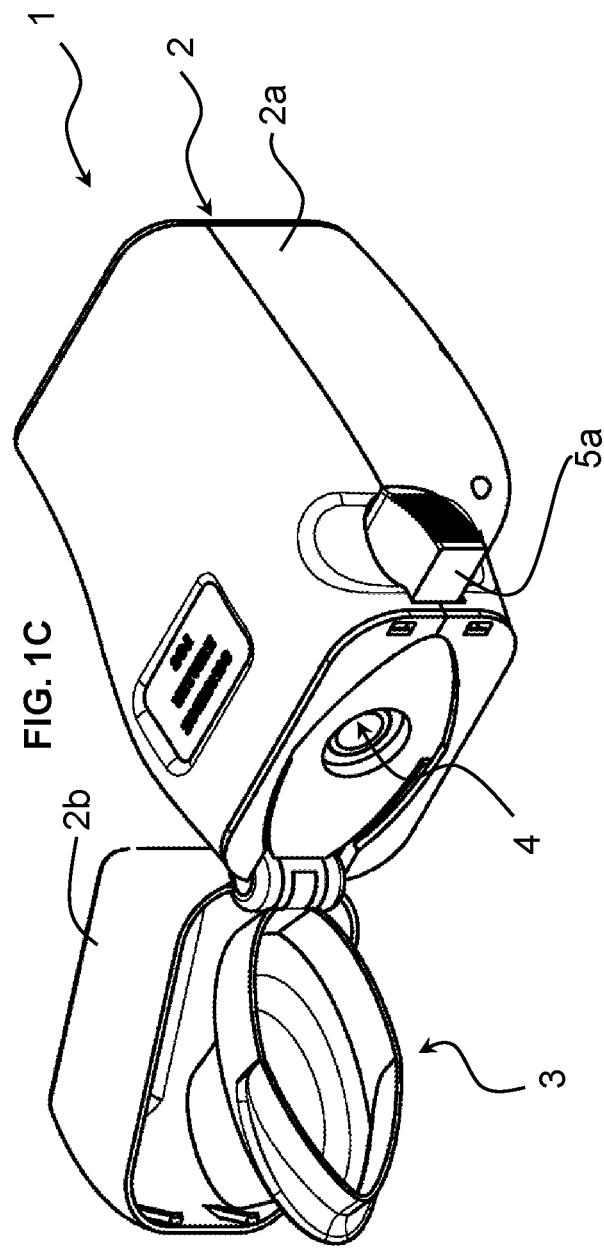

INHALER

CROSS-REFERENCE TO RELATED APPLICATIONS

The present application is a national stage entry of International (PCT) Patent Application Number PCT/EP2019/061712, filed May 7, 2019, which in turn claims priority to European Patent Application No. 18171361.1, filed May 8, 2018, the subject matter of which are expressly incorporated herein by reference.

The present invention relates to an inhaler for administration of a drug by inhalation, in particular for administration of a drug in dry powder form.

It is known to provide a medicament in the form of a dry powder contained in a capsule. The capsule is placed in a compartment of an inhaler device comprising perforating means to perforate the capsule. The capsule compartment is positioned in an airflow passage, the airflow serving to disaggregate the dry powder and blow it out of a mouthpiece of the inhaler.

Conventional inhalers include passive devices in which the airflow is generated solely by the patient breathing in through the mouthpiece. Active devices comprising an air pump that assists flow of air through the drug capsule are also known. Conventional inhaler devices however all rely on a patient breathing in with a certain flow rate in order to ensure that the drug enters into the patient's lungs. The active air pump provided in the inhaler device is used for disaggregation and mixing of the drug particles with air to improve dispersion and thus absorption of the drug.

Certain patients however have very limited breathing capacity, and patients that have sufficient breathing capacity may also not breath from the inhaler device in an optimal manner for the drug to enter deeply into the patient's lungs. Conventional inhaler devices rely on a minimum inhalation inflow over a certain time exerted by the patient for optimal efficacy. Due to different patient conditions, or due to improper use, there may be many circumstances in which a drug for inhalation is not properly administered.

In view of the above, it is an object of this invention to provide an inhaler that optimizes inhalation of a drug, for patients that have respiratory difficulties or that do not inhale deeply enough or fully enough.

It is advantageous to provide an inhaler for administration of a drug that is compact and easy to carry around.

It is advantageous to provide an inhaler for administration of a drug in dry powder form that ensures good disaggregation of the powder and good mixing and dispersion of the powder particles in the air to be inhaled by the patient.

It is advantageous to provide an inhaler for administration of a drug that is convenient and easy to use and that is discreet.

It is advantageous to provide an inhaler device for administration of a drug that is economical to produce and that has a high autonomy.

Objects of this invention have been achieved by providing the inhaler for administration of a drug as set forth in claim 1.

Disclosed herein is an inhaler for oral inhalation administration of a drug, comprising a housing, a drug chamber in the housing, and an air pump configured to pump air through the drug chamber for expulsing the drug through an outlet of a mouthpiece. The air pump comprises a motor coupled to a centrifugal compressor turbine. Advantageously the centrifugal compressor turbine allows to provide both sufficient pressure and airflow rate for optimal administration of an inhaled drug deep into a patient's lung.

The air pump is operable to pump air through the drug chamber at a pressure greater than 20 millibars and a flow rate greater than 20 litres per minute.

In an advantageous embodiment, the air pump is operable to pump air through the drug chamber at a pressure greater than 30 millibars and a flow rate greater than 25 litres per minute, preferably at a pressure greater than 35 millibars and a flow rate greater than 30 litres per minute, for instance about 40 millibars at a flow rate about 35 l/min.

In an advantageous embodiment, the motor comprises a stator with a plurality of coils mounted on a coil support and a rotor comprising an axis and a permanent magnet core with a plurality of magnetic poles, the stator coil support being formed of a non-ferromagnetic material.

In an advantageous embodiment, the coil support may be made of polymer.

In an advantageous embodiment, the stator coil support may be formed of an integrally moulded plastic part.

In an advantageous embodiment, the stator comprises three coils.

In an advantageous embodiment, the air pump comprises a casing comprising a tubular circumferential channel surrounding a turbine of the compressor, the tubular channel fluidly connected to an outlet channel that is fluidly connected and adjacent an inlet of the drug chamber.

In an advantageous embodiment, the outlet channel of the compressor is tangential to the tubular circumferential channel and aligned with a through-flow axis of the drug chamber.

In an embodiment, the air inlet of the air pump is co-axial with the axis of the rotor.

In an advantageous embodiment, the rotor axis of the air pump is orthogonal to a general direction of flow of air through the drug chamber and mouthpiece outlet.

In an advantageous embodiment, the motor of the air pump is coupled directly to a turbine of the compressor operable to rotate at a speed exceeding 100000 rpm, preferably exceeding 120000 rpm.

In an advantageous embodiment, the inhaler comprises a pressure sensor arranged in an airflow channel between an outlet of a mouthpiece and an outlet channel of the air pump.

The outlet pressure sensor is coupled to a control circuit of a drive of the air pump and may be used to actuate operation of the air pump.

The pressure sensor may be operable to detect a negative pressure representative of a patient inhaling, to actuate operation of the air pump.

In an advantageous embodiment, the pressure sensor is connected in a regulation loop via the control circuit to the drive of the air pump configured to control the speed of the motor of the air pump such that an outlet pressure follows a pressure profile stored in a memory of the control circuit or computed by the control circuit.

In an embodiment, the pressure sensor may also be used to monitor inhalation pressure during a calibration step to adjust the air pump pressure and flow rate as a function of the patient's respiratory capability.

In an embodiment, the inhaler further comprises a capsule perforator comprising perforator needles actionably insertable into the drug chamber for piercing a drug capsule positioned in the drug chamber.

In an embodiment, the inhaler is configured for receiving a capsule containing a drug in a dry powder form therein for administration of the drug into a patient's lungs by inhalation.

In an advantageous embodiment, a rotor of the motor is supported in rotation relative to the stator by an air bearing.

Also disclosed herein is a method of operating an inhaler as set forth herein, comprising monitoring a negative inhalation pressure of a patient via a pressure sensor, and adjusting the pressure and flow rate of the air pump as a function of the monitored pressure.

The pressure may be adjusted according to a constant value.

In a variant, the pressure may be adjusted according to a profile of values as a function of time or of volume of air pumped.

In a variant, the pressure may be adjusted according to a value computed by an algorithm in the control circuit based on a measurement of the patient's inhalation capacity.

Further objects and advantageous features of the invention will be apparent from the claims and the following detailed description of embodiments of the invention in relation to the annexed drawings in which:

FIG. 1a is a perspective view of an inhaler for administration of a drug according to an embodiment of the invention;

FIG. 1b is a perspective view of the inhaler of FIG. 1a with a cap thereof in an opened position;

FIG. 1c is a view similar to FIG. 1b, showing a cap and a mouthpiece in an opened position allowing insertion of a drug capsule in the device;

FIG. 3a is a cross-sectional view of the embodiment of FIG. 1b;

FIG. 3b is a detailed partial view of FIG. 3a;

FIG. 4a is top plane view of an air pump of an inhaler according to an embodiment of the invention;

FIG. 4b is a cross-sectional view through lines IVb-IVb of FIG. 4a;

FIG. 4c is an exploded perspective view of the air pump of FIG. 4a;

FIG. 5a is a perspective view of a motor of the air pump according to an embodiment of the invention;

FIG. 5b is a cross-sectional view of the motor of FIG. 5a;

FIG. 6a is a perspective view of a motor of the air pump according to another embodiment of the invention;

FIG. 6b is a cross-sectional view of the motor of FIG. 6a;

Figure 2:
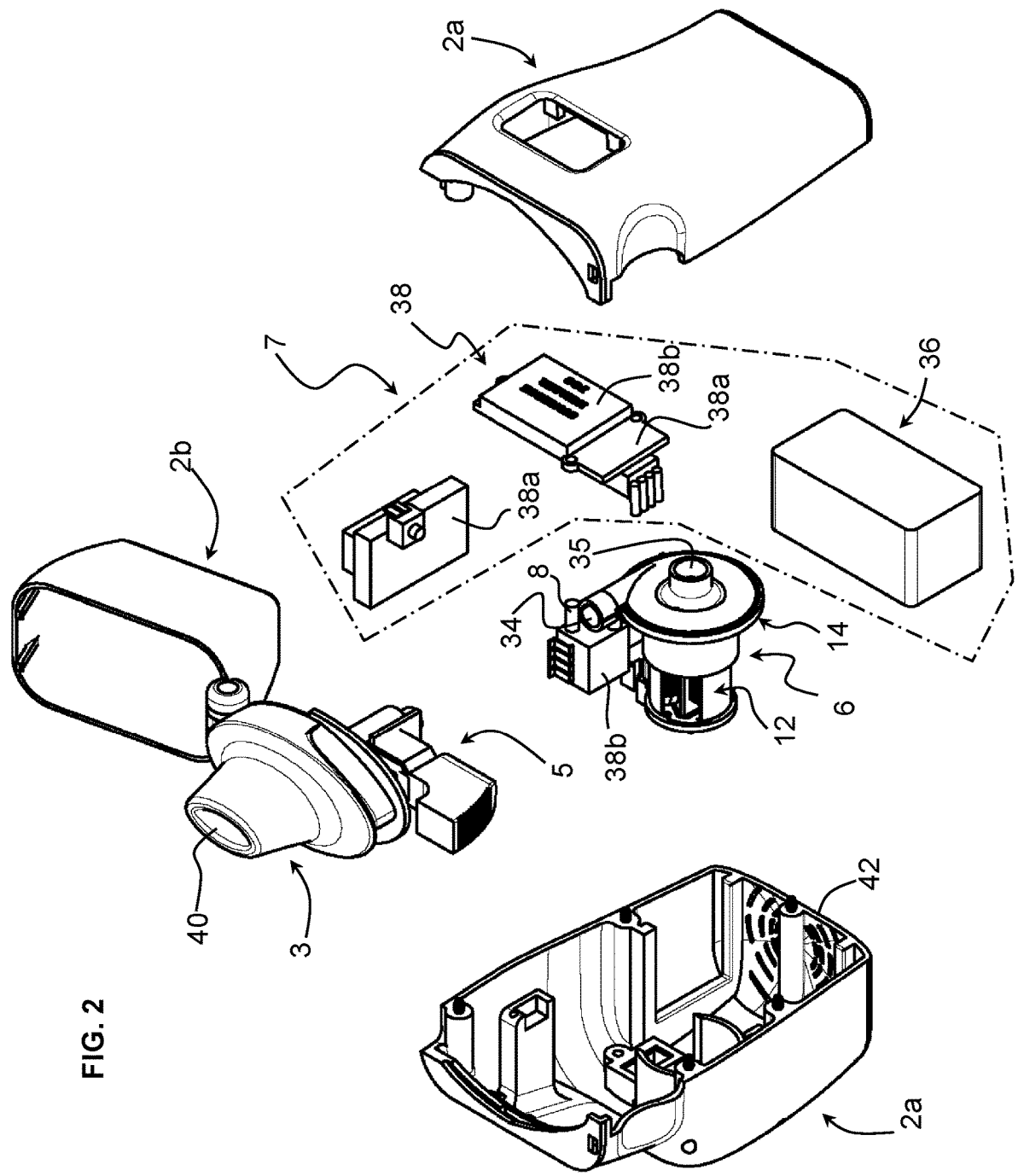
FIG. 2 is a perspective exploded view of the embodiment of FIG. 1b.
Figure 3:
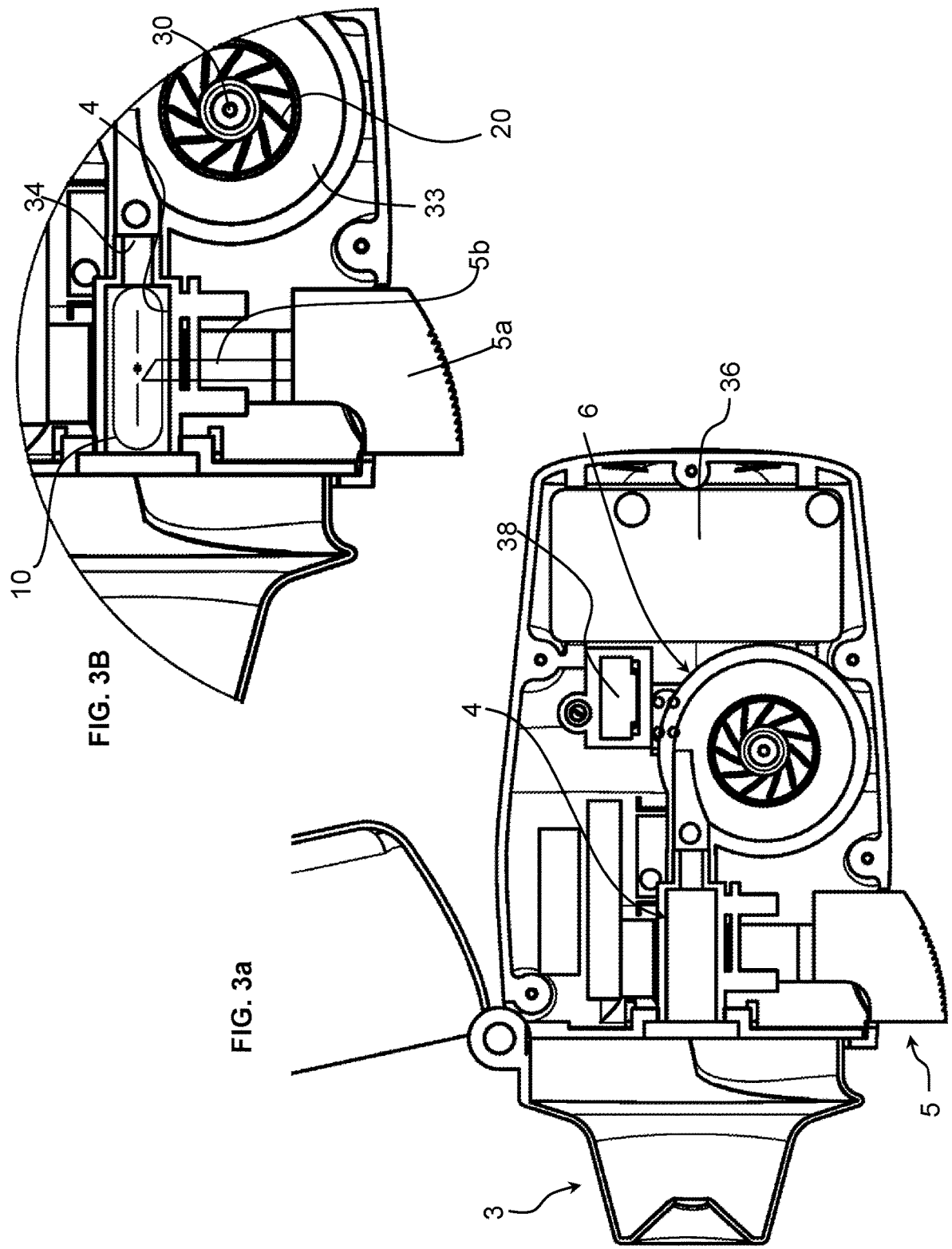
Figure 4:
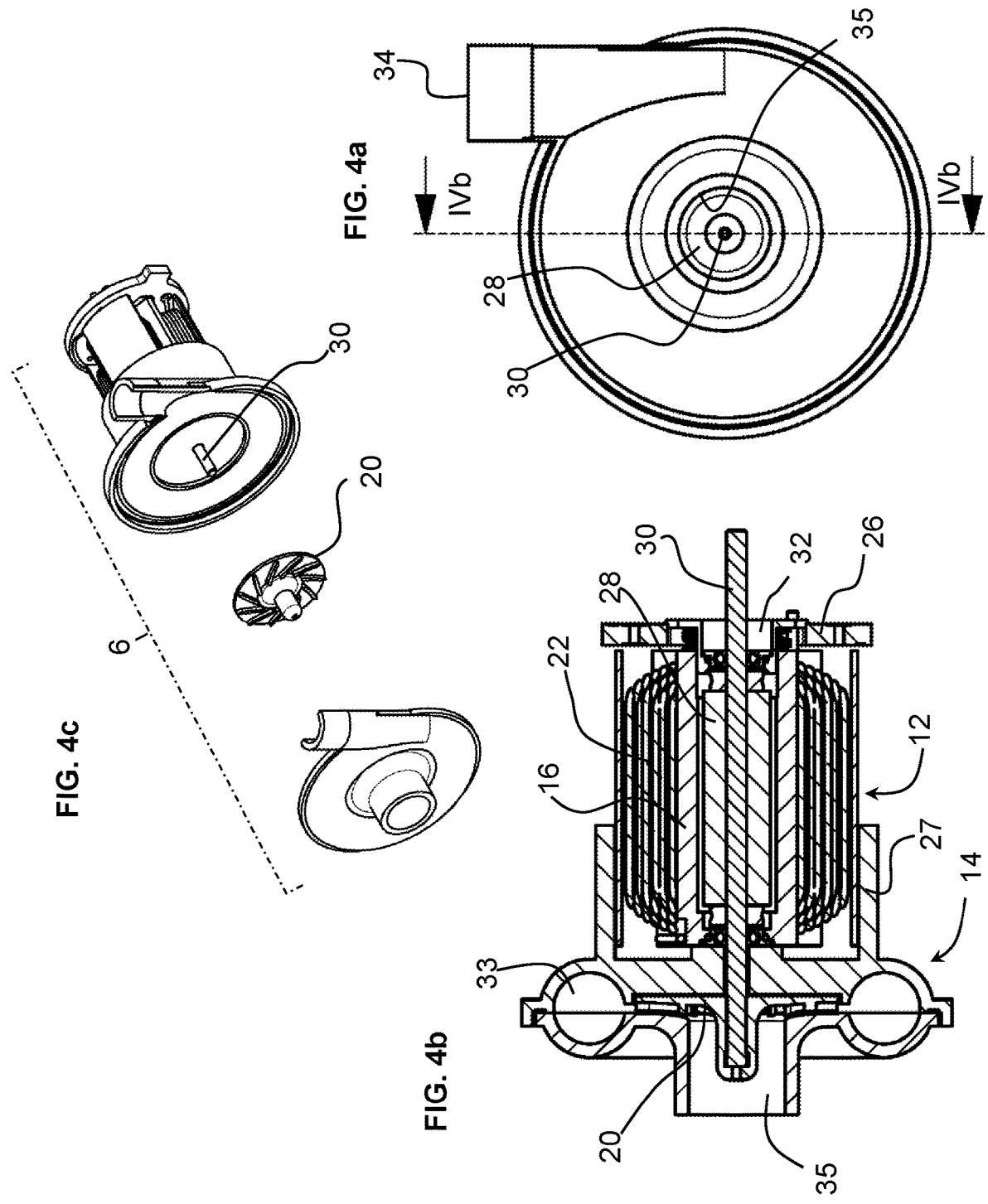

Referring to the figures, an inhaler 1 according to embodiments of the invention comprises a housing 2, a drug chamber 4 for receiving a medication capsule therein within the housing, an air pump 6 mounted within the housing configured to blow air through the drug chamber, a drive 7 for controlling and driving the air pump 6, a mouthpiece 3 for interfacing with a patient's mouth, and optionally a pressure sensor 8 configured to detect negative pressure due to inhalation by a patient in order to actuate the air pump.

The housing 2 in the illustrated embodiment comprises a base portion 2a and a cap portion 2b that in this example is pivotally connected to the base portion to cover a mouthpiece when the inhaler is not in use and to allow access to the mouthpiece during use. The mouthpiece 3 may also be pivotally connected to the base portion 2a of the housing in order to allow access to the drug chamber 4 for loading of a drug in the drug chamber 4, or for unloading a used capsule or other drug container after administration of the drug. The drug may in particular be in the form of a dry powder contained in a sealed capsule 10. The sealed capsule is configured to be perforated in order to allow airflow through the capsule and extraction of the dry powder from the capsule. Such dry powder capsules are per se known and the principle of perforating the capsule and passing air therethrough are also known per se. Within the scope of the invention it is however possible to provide the drug in other container forms such as in a frangible container or in a container having pre-formed orifices with valve elements.

The invention may also be used for a drug container containing a liquid drug, whereby the air flow through the container nebulizes the liquid into fine droplets.

A bottom wall 42 of the housing base portion 2a comprises an air inlet 44 allowing air to flow into the air pump 6. The pumped air passes through the drug chamber 4 and projects out of the outlet 40 of the mouthpiece 3.

The inhaler may further comprise a capsule perforator 5 to perforate the drug capsule 10 positioned in the drug chamber 4.

In the illustrated embodiment, the capsule perforator 5 comprises a push button 5a, which may for instance comprise a spring to keep it in the unactuated position, connected to perforator needles 5b that are configured to pierce the capsule envelope when the push button 5a is pressed. The perforator needles may typically comprise a pair of perforator needles 5b to pierce holes proximate opposed ends of the drug capsule. Air flowing through the drug chamber 4, upon actuation of the air pump 6, flows through the perforation holes to draw the dry powder therein out of the capsule.

For optimal evacuation of the dry powder from the capsule and good disaggregation, it is advantageous that a certain pressure threshold is exceeded, preferably greater that 25 millibars, more preferably greater than 35 millibars, for instance around 40 millibars.

Figure 7:
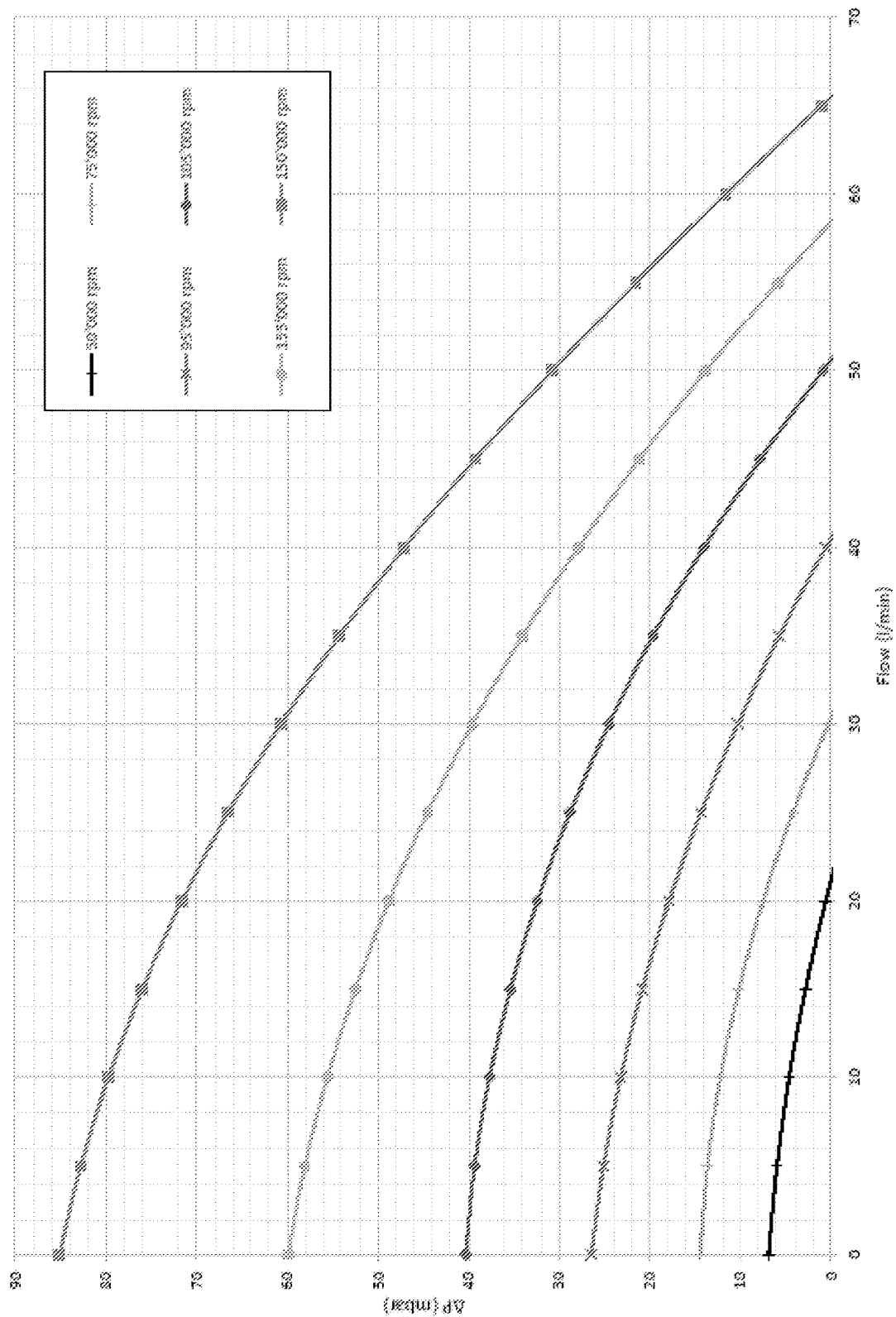
FIG. 7 is a graph of pressure difference (Y axis) and flow rate (X axis) of an air pump according to embodiments of the invention.

The air pump 6 according to an embodiment of the invention comprises a motor 12 coupled to a compressor 14 comprising a turbine 20, configured as a centrifugal air pump. To ensure both good disaggregation and expulsion of the drug in the drug chamber 4, and deep penetration of the drug into a patient's lung, the motor and compressor are configured to generate a pressure greater than 20 mbars (millibars) at a flow rate greater than 20 l/min (litres per minute), preferably a pressure greater than 30 mbars at a flow rate greater than 25 l/min, more preferably a pressure greater than 35 mbars at a flow rate greater than 30 l/min, for instance around 40 mbars at a flow rate of 35 l/min. As illustrated in FIG. 7, the pump generated pressure and flow rate are substantially inversely proportional. In examples of the invention, with an embodiment of a centrifugal air pump having dimensions that fit into a handheld inhaler as illustrated in FIGS. 1a to 1b, a centrifugal compressor turbine rotating at 100,000 rpm generates about 20 mbar pressure for a flow rate about 17 l/min, whereas a centrifugal compressor turbine rotating at 130,000 rpm generates about 40 mbar pressure for a flow rate about 35 l/min.

A flow rate of around 30 to 40 l/min provides assistance to patients with respiratory difficulties that ensures that the medication is inhaled deeply into the patient's lung even if the inhalation pressure provided by a patient is very poor. For children, a flow rate of around 20 to 30 l/min may be more appropriate to ensure optimal deposition into the lung.

Depending on the inhalation strength of patients like children with a developing lung function, the compressor turbine may have to generate more pressure compared to adults. For example, at a flow rate of 30 l/min, a pressure of around 35 mbar may be required for an adult whereas a pressure of around 50 mbar may be required for children.

The pressure required to achieve a given flow rate through the inhaler further depends on the specific design of the drug chamber. A high-resistance drug chamber will require a higher pressure by the compressor turbine than a low-resistance drug chamber.

Advantageously, the use of a centrifugal air pump at very high rotational speed allows to provide both the high pressure differential and the high flow rate in a very compact arrangement.

Moreover, the ability to provide both the high pressure differential and the high flow rate leads to a large flexibility in the range of operational parameters, in particular for a dynamic regulation of the flow rate and pressure as a function of the selected operating mode for the chosen application.

The motor 12 comprises a stator 16 and a rotor 18 having an axis 30 coupled to the compressor turbine 20. The rotor core 28 comprises a multipole permanent magnet mounted on the axis, rotating within the stator 16 and supported by bearings 32, 32'. The stator 16 comprises a plurality of coils 22 mounted on a coil support 24. The stator may further be coupled to a mounting base 26 and further comprise a casing or housing 27.

The bearings may in a first embodiment be in the form of ball bearings 32. In another embodiment, the bearings are in the form of air bearings 32'. A film of air forms between the rotor portion 32'*a* and the stator tube portion 32'*b* at high rotation speeds and provides a gaseous separation between the rotor and stator. Air bearings are advantageous at very high rotation speeds, for instance above 50000 RPM, ensuring very low friction, low heat loss and low noise. Another advantage is that air bearings do not need lubrication, thereby minimising the risk of air path contamination. This is particularly relevant since the air is inhaled by the patient. Moreover, the assembly cost of the device is lowered and may be made more compact than with ball or roller bearings. The configuration of air bearings are per se known in other fields and need not be described in more detail herein.

The casing 27 of the compressor portion comprises a tubular annular channel 33 arranged around the turbine 20 for collecting the centrifugally projected air, the tubular annular channel 33 leading tangentially to an outlet channel 34 connected fluidly to the drug chamber 4. The outlet channel may be aligned with the air through-flow axis of the drug chamber 4 and the axis 30 of the motor may be orthogonal to said air through-flow axis for a compact arrangement.

The air inlet 35 of the compressor 14 is co-axial with the center axis 30 and may open into the inside of the housing 2 whereby the air inlets 44 on the bottom wall 42 (shown in FIG. 1*a*) allow air to be drawn into the housing 2. It may be noted however that the air inlet 44 may be in various positions on the housing and not necessarily on or only on the base wall. Moreover, the air inlet may be provided with a particle filter to prevent dust from entering into the pump as air is drawn into the housing 2.

The coil support 24 of the stator 16 according to a preferred embodiment of the invention may be made of a material without a magnetic core or yoke (i.e. a coreless stator), for instance of a polymer or a composite polymer material. Advantageously, although the absence of a magnetic core reduces the magnetic coupling between the motor coils 22 and the rotor core 28, at very high rotational speeds advantageous for driving the centrifugal air pump 6, the loss of magnetic coupling is offset by the absence of iron losses (hysteresis and eddy current losses) that increase with rotational speed in a motor with a stator magnetic core. Thus, at the preferred rotational speeds over 100000 rpm or more, the motor generates less losses and thus produces more power than a comparable motor with a standard industrial ferromagnetic stator core, like silicon-iron lamination stack. Moreover, in the absence of a magnetic core, for a given diameter there is also more volume available for the coil windings, thus leading to a higher power to size and/or power to weight ratio compared to a motor with a standard industrial ferromagnetic stator core. The coreless stator also enables a more economical manufacturing of the stator which may be made of a moulded injected or extruded plastic material in a single integral piece.

Figure 5:
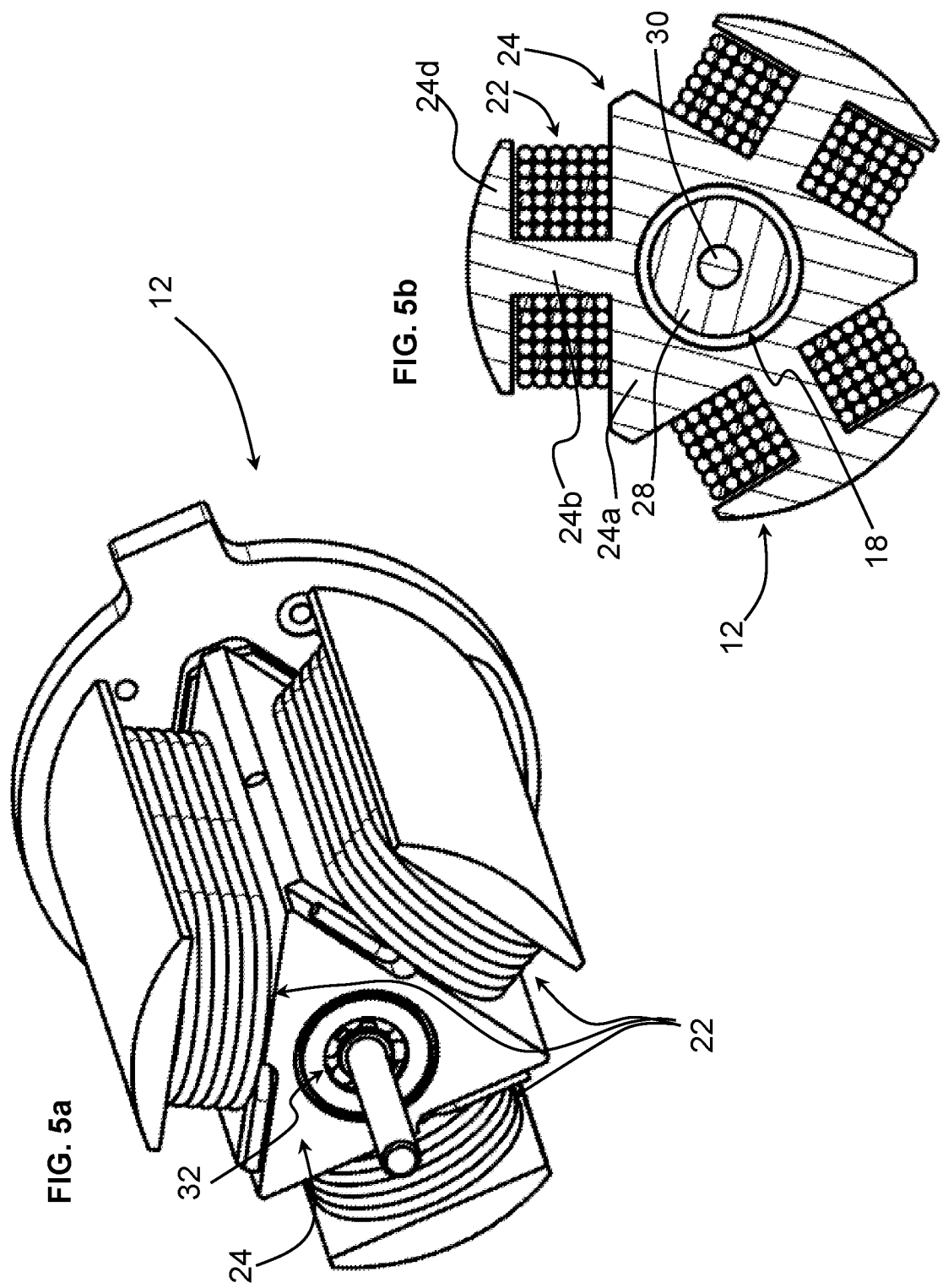
Figure 6:
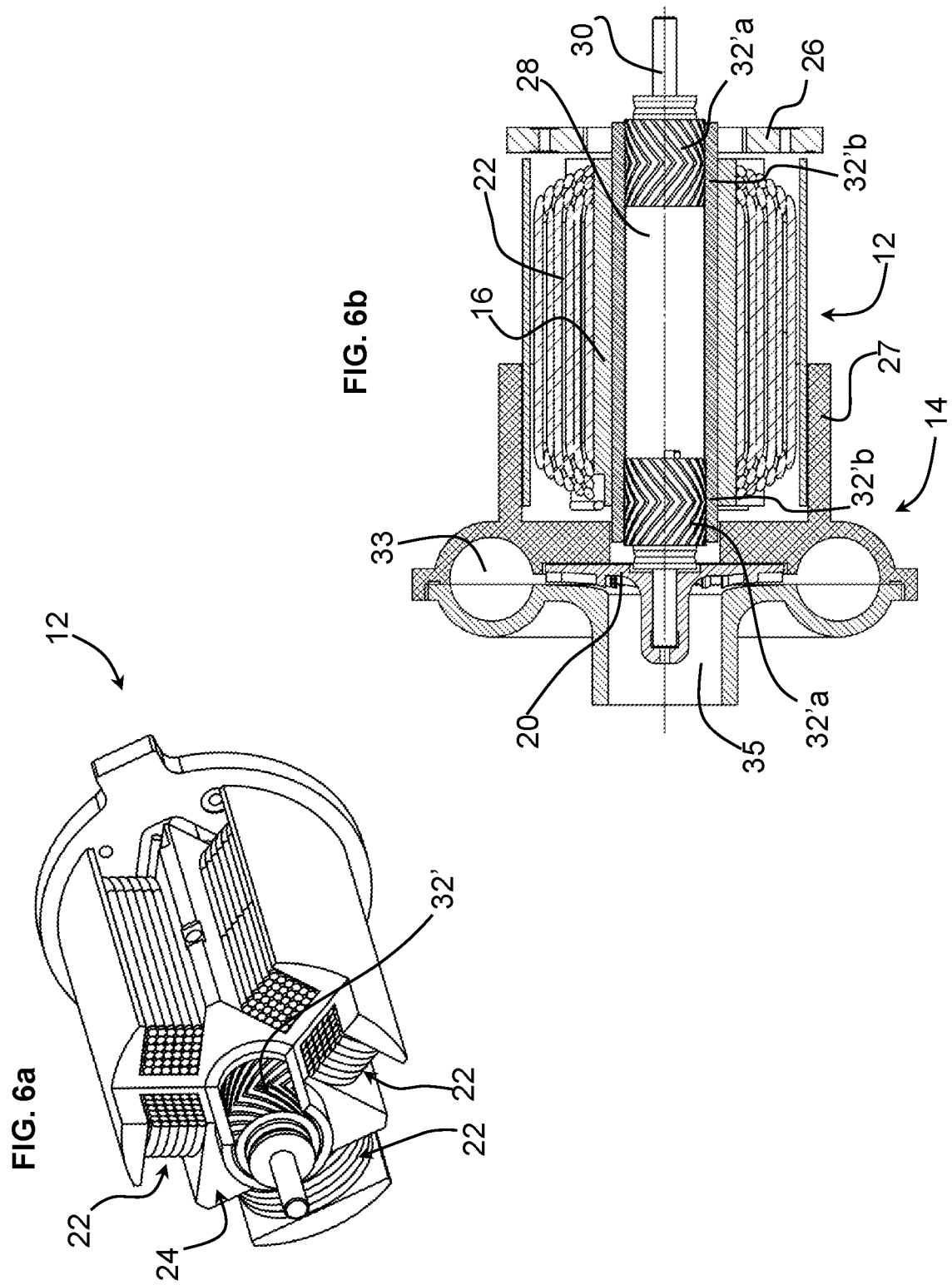

In an advantageous embodiment, the stator comprises three coils 22 arranged symmetrically around the center axis 30 of the motor, each coil mounted on a radial arm 24*b* extending from a center portion 24*a* of the coil support. The center portion may for instance have a substantially triangular shape in cross-section as illustrated in FIG. 5*b*, with flanges 24*d* at an outer end of the radial arms 24*b* to contain the coils.

The air pump is controlled by a drive 7 which comprises a power supply that may be in the form of a battery 36, and a control circuit 38, for instance comprising a circuit board 38*a* and circuit components 38*b* including at least a microprocessor 39 for controlling operation of the air pump.

The outlet pressure sensor 8 may advantageously be positioned within the air flow passage between the outlet 40 of the mouthpiece and the outlet channel 34 of the air pump 6, for instance at an outlet end of the drug chamber. The pressure sensor 8 is configured to sense a negative pressure due to inhalation by a patient to trigger actuation of the air pump for administration of the drug. Actuation of the inhaler may advantageously require a second command, for instance a switch actuated by a user (patient, healthcare practitioner or other assisting person) that switches the outlet pressure sensor actuation on. The pressure sensor ensures that the administration of the drug is performed only once the patient has actuated the inhaler and starts inhaling.

In an embodiment, when the patient inhales via the mouthpiece, the negative inhalation pressure may be monitored via the pressure sensor and the control circuit is operable to adjust the pressure and flow rate of the air pump as a function of the monitored pressure.

This enables for instance the air pump to be operated in order to compensate for insufficient inhalation of air by a patient with respiratory difficulty. The monitoring may be performed in a calibration step prior to administration of the drug, or dynamically during administration of the drug.

In an embodiment with a calibration step, once the monitoring is finished, the inhaler may indicate to the patient, via a user interface of the device, to inhale deeply and by doing so this will activate the turbine and generate the right amount of air flow to push correctly the drug deeply into the patient lungs.

This feature enables to adapt the airflow and pressure to the correct level for optimal administration state as a function of the state of the patient at the time of administration.

Monitoring of the pressure in the air flow passage between the outlet 40 of the mouthpiece and the outlet channel 34 of the air pump 6 may be performed by one or more sensors in one or more positions along the air flow passage.

Figure 8A:
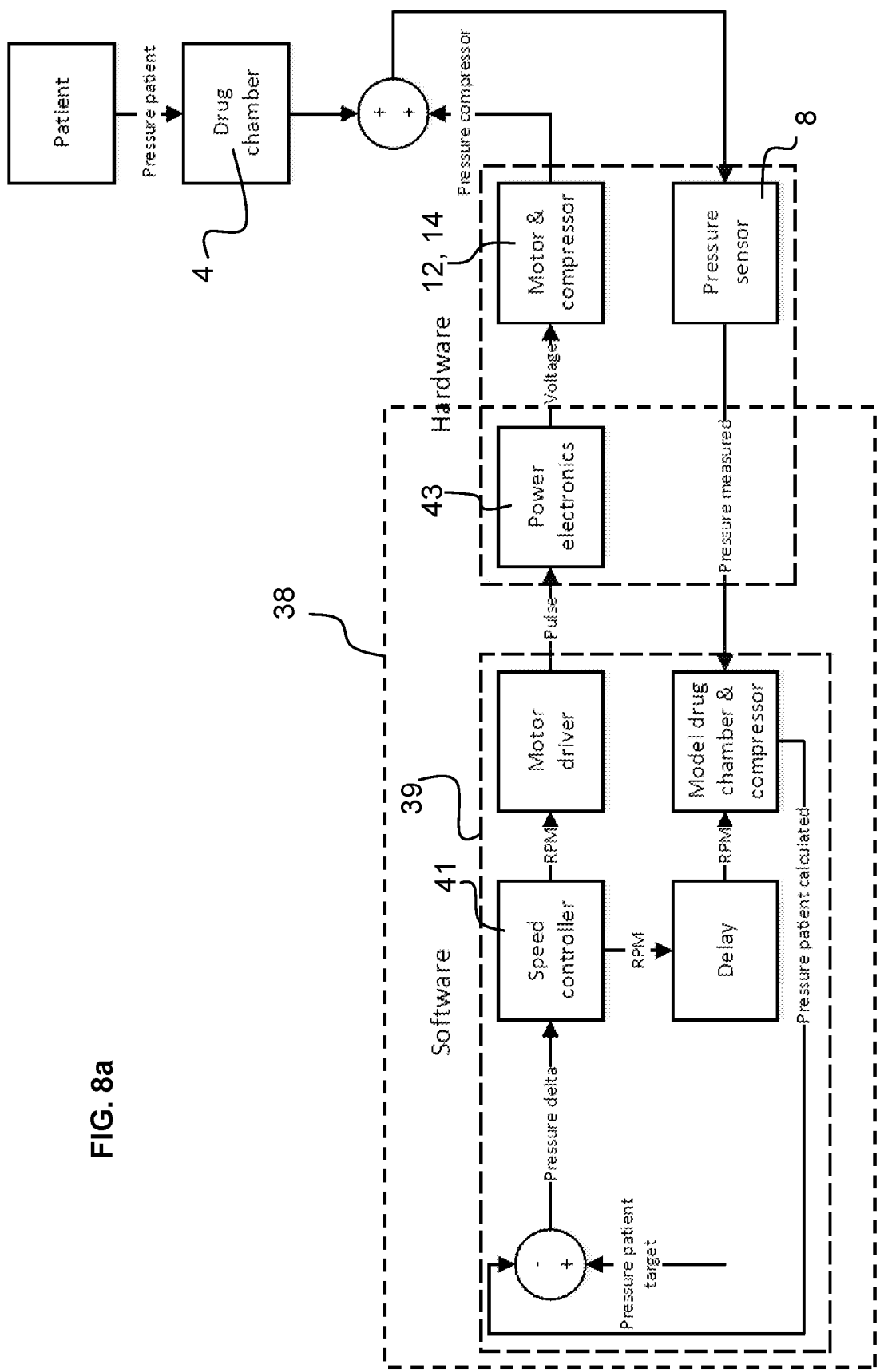
FIG. 8a is a schematic flowchart illustrating a method of operation of the air pump according to a first embodiment of the invention.
Figure 8B:
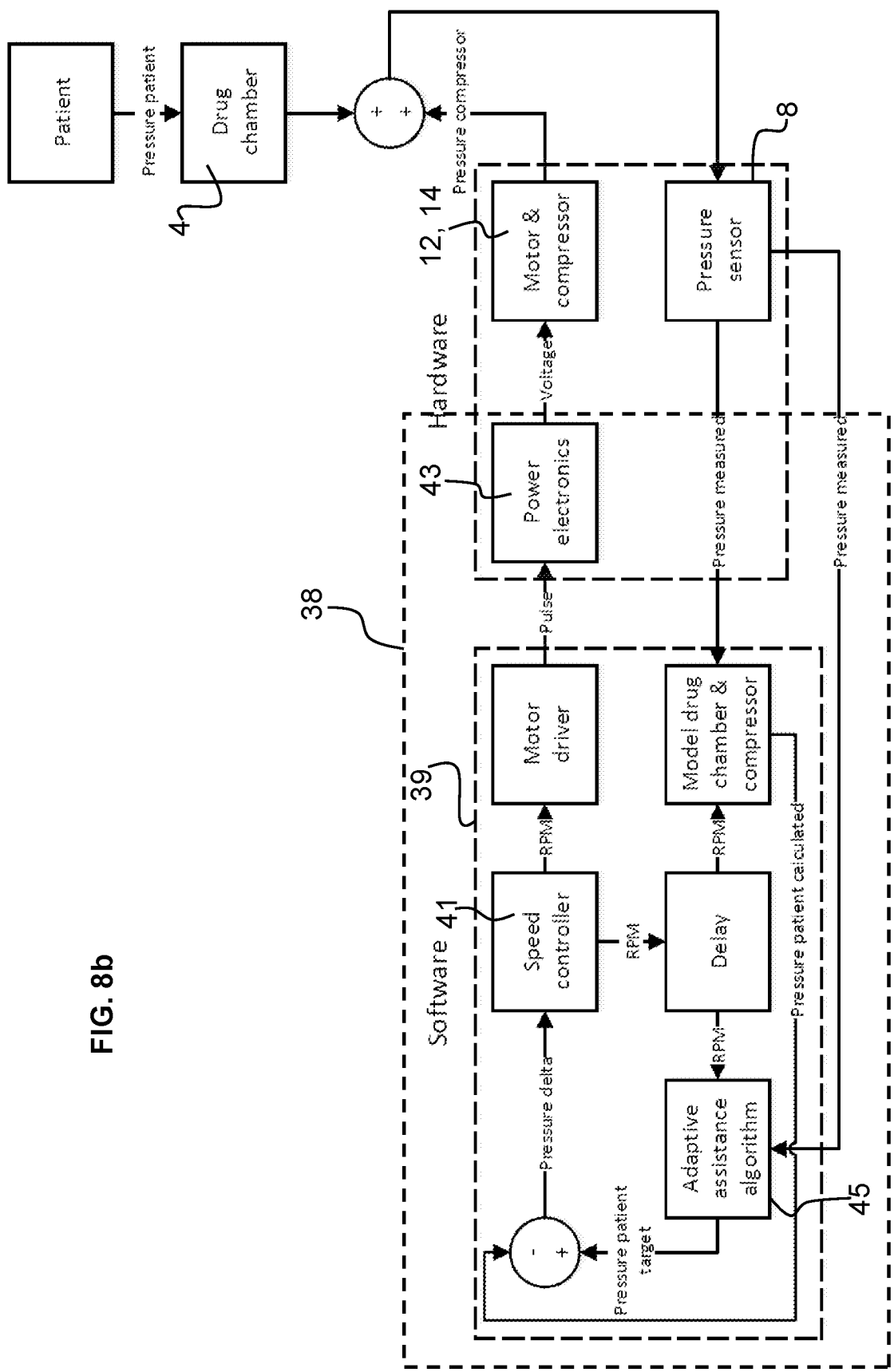
FIG. 8b is a schematic flowchart illustrating a method of operation of the air pump according to a second embodiment of the invention.

The sensor(s) monitoring of the pressure in the airflow passage and/or at the outlet of the mouthpiece may be connected to the control circuit in a regulation loop as illustrated in the embodiments of FIGS. 8a and 8b.

In a first embodiment illustrated in FIG. 8a, the pressure measured by the pressure sensor 8 in the air flow passage, for instance at the outlet, is used to regulate the speed of the motor 12 of the air pump 6 in a feed-back (regulation) loop. Algorithms in a microprocessor 39 of the control circuit 38 receive the pressure measurement signal and based on a target pressure output ("pressure patient target") calculates a difference that is fed to a speed controller algorithm 41 that generates a motor drive speed signal transmitted to power electronics 43 of the control circuit connected to the motor 12.

The target pressure for the patient ("pressure patient target") may for instance be a constant value or a set pressure profile that may be set at atmospheric pressure, or below atmospheric pressure, or in certain configurations above atmospheric pressure.

When the pressure patient target is set at atmospheric pressure, for patients with weak natural inhalation capacity, this provides a comfortable sensation and ensures that patient can draw the drug particles deep into the patient's lungs. For patients with particularly severe conditions, the pressure may be set at slightly higher than atmospheric pressure in order to provide assistance to inhalation in a positive manner. A slightly negative pressure may also be set for a patient where a sensation of "breathing in" is preferred whereby the patient has a sensation of more control of the inhalation process.

The set pressure profile may have a value that varies as a function of time or as a function of the volume of air inhaled, such that for instance in the initial inhalation process the pressure may be greater than towards a mid or final stage of the inhalation process.

In another embodiment as best illustrated in FIG. 8b, the algorithm may be configured to determine the pressure patient target as a function of the patient's inhalation pressure. Thus, for very low patient inhalation pressures that may be associated to very severe patient breathing problems, the patient target may be set at a different level than for patients generating a higher negative inhalation pressure. An adaptive assistance algorithm 45 that receives the measured pressure from the pressor sensors may thus be used to calculate an optimal patient pressure target that may then be used to control the speed of the motor via the power electronics receiving a motor driver signal as already described above.

List of references

Inhaler 1
Housing 2
Base portion 2a
Bottom wall 42
Air inlet 44
Cap portion 2b
Mouthpiece 3
Outlet 40
Drug chamber 4
Capsule perforator 5
Actuation button 5a
spring
Perforator needles 5b -continued List of references Air pump 6
Motor 12
Stator 16
Coil 22
Coil support 24
Centre portion 24a
Radial arms 24b
Flange 24d
Mounting Base 26
Air bearing support 32'b
Rotor 18
Core 28
(Permanent magnet - segmented)
Axis 30
Bearing 32
Air bearing 32', 32'a
Compressor 14
Turbine 20
Outlet channel 34
Tubular annular channel 33
Casing 27
Drive 7
Power supply (battery) 36
Control circuit 38
Circuit board 38a
Circuit components 38b
Microprocessor 40
Pressure sensor 8 (e.g. outlet pressure sensor)

The invention claimed is:

1. An inhaler for oral inhalation administration of a drug, comprising a housing, a drug chamber in the housing, an air pump in the housing upstream of the drug chamber configured to pump air through the drug chamber for expulsing the drug through an outlet of a mouthpiece, and a capsule perforator comprising perforator needles actionably insertable into the drug chamber for piercing a drug capsule positioned in the drug chamber, wherein the air pump comprises a motor coupled to a centrifugal compressor operable to pump air through the drug chamber at a pressure greater than 20 millibars and a flow rate greater than 20 litres per minute.

2. The inhaler according to claim 1, wherein the motor is operable to rotate at a speed exceeding 100,000 rpm.

3. The inhaler according to claim 2, wherein the air pump is operable to pump air through the drug chamber at a pressure greater than 30 millibars and a flow rate greater than 25 litres per minute.

4. The inhaler according to claim 3, wherein the air pump is operable to pump air through the drug chamber at a pressure greater than 35 millibars and a flow rate greater than 30 litres per minute.

5. The inhaler according to claim 1, wherein the motor comprises a stator with a plurality of coils mounted on a coil support and a rotor comprising an axis and a permanent magnet core with a plurality of magnetic poles, the stator coil support being formed of a non-ferromagnetic material.

6. The inhaler according to claim 5, wherein the coil support is made of polymer.

7. The inhaler according to claim 5, wherein the stator coil support is formed of an integrally moulded plastic part.

8. The inhaler according to claim 5, wherein the stator comprises three coils.

9. The inhaler according to claim 1, wherein the air pump comprises a casing comprising a tubular circumferential channel surrounding a turbine of the compressor, the tubular channel fluidly connected to an outlet channel that is fluidly connected and adjacent an inlet of the drug chamber.

10. The inhaler according to claim 9, wherein the outlet channel of the compressor is tangential to the tubular circumferential channel and aligned with a through-flow axis of the drug chamber.

11. The inhaler according to claim 1, wherein an air inlet of the air pump is co-axial with an axis of a rotor.

12. The inhaler according to claim 1, wherein a rotor axis of the air pump is orthogonal to a general direction of flow of air through the drug chamber and mouthpiece outlet.

13. The inhaler according to claim 1, wherein the motor of the air pump is coupled directly to a turbine of the compressor operable to rotate at a speed exceeding 120,000 rpm.

14. The inhaler according to claim 1, wherein a rotor of the motor is supported in rotation by a stator of the motor via an air bearing.

15. The inhaler according to claim 1, further comprising a pressure sensor arranged in an airflow channel between the outlet of the mouthpiece and an outlet channel of the air pump, the pressure sensor coupled to a control circuit of a drive of the air pump.

16. The inhaler according to claim 15, wherein the pressure sensor is operable to detect a negative pressure representative of a patient inhaling, to actuate operation of the air pump.

17. The inhaler according to claim 15, wherein the pressure sensor is connected in a regulation loop via the control circuit to the drive of the air pump configured to control the speed of the motor of the air pump such that an outlet pressure follows a pressure profile stored in a memory of the control circuit or computed by the control circuit.

18. The inhaler according to claim 1, configured for receiving a capsule containing a drug in a dry powder form therein for administration of the drug into a patient's lungs by inhalation.

19. A method of operating an inhaler according to claim 1, comprising monitoring a pressure in the airflow passage between the air pump and the outlet via a pressure sensor, and adjusting the pressure and flow rate of the air pump as a function of the monitored pressure.

20. The method according to claim 19, wherein the pressure is adjusted according to a constant value.

21. The method according to claim 19, wherein the pressure is adjusted according to a constant profile of values as a function of time or of volume of air pumped.

22. The method according to claim 19, wherein the pressure is adjusted according to a value computed by an algorithm in a control circuit based on a measurement of a patient's inhalation capacity.

* * * * *